United States Patent
Wenzel et al.

(10) Patent No.: US 7,756,586 B2
(45) Date of Patent: Jul. 13, 2010

(54) WOUND HEALING PATCH WITH GUARD ELECTRODES

(75) Inventors: Stuart Wenzel, San Carlos, CA (US); Mariam Maghribi, Fremont, CA (US); Mark Huang, Pleasanton, CA (US)

(73) Assignee: Lifescan, Inc., Milpitas, CA (US)

( * ) Notice: Subject to any disclaimer, the term of this patent is extended or adjusted under 35 U.S.C. 154(b) by 262 days.

(21) Appl. No.: 11/876,134

(22) Filed: Oct. 22, 2007

(65) Prior Publication Data

US 2008/0103549 A1 May 1, 2008

Related U.S. Application Data

(60) Provisional application No. 60/863,417, filed on Oct. 30, 2006.

(51) Int. Cl.
*A61N 1/04* (2006.01)
(52) U.S. Cl. ..................................................... 607/50
(58) Field of Classification Search .................. 607/50, 607/46, 142, 115, 129; 600/382, 383, 384, 600/393
See application file for complete search history.

(56) References Cited

U.S. PATENT DOCUMENTS

| 4,142,521 A | 3/1979 | Konikoff |
| 4,982,742 A | 1/1991 | Claude |
| 5,295,482 A * | 3/1994 | Clare et al. .................. 600/385 |
| 5,395,398 A | 3/1995 | Rogozinksi |
| 5,520,683 A * | 5/1996 | Subramaniam et al. ....... 606/32 |
| 5,974,344 A | 10/1999 | Shoemaker, II |
| 6,235,047 B1 | 5/2001 | Augustine et al. |
| 6,411,853 B1 | 6/2002 | Millot et al. |
| 2004/0015223 A1 * | 1/2004 | Andino et al. .............. 607/142 |
| 2005/0043658 A1 | 2/2005 | Rix |
| 2005/0244484 A1 | 11/2005 | Flick |
| 2006/0052678 A1 | 3/2006 | Drinian et al. |
| 2006/0189912 A1 | 8/2006 | Gabaret |
| 2008/0027509 A1 * | 1/2008 | Andino et al. ................. 607/50 |

FOREIGN PATENT DOCUMENTS

WO WO 2005/099644 A2 10/2005
WO WO 2006/089377 A1 8/2006

OTHER PUBLICATIONS

U.S. Appl. No. 60/863,433, filed Oct. 30, 2006, Wenzel.
U.S. Appl. No. 60/863,425, filed Oct. 30, 2006, Wenzel.

* cited by examiner

*Primary Examiner*—Carl H Layno
*Assistant Examiner*—Frances P Oropeza

(57) ABSTRACT

In one example, the present invention is directed to a wound-healing patch including a flexible substrate, at least one wound electrode, at least one guard electrode and at least one return electrode. The guard electrode is positioned between the wound and return electrodes in the electrical path of current traveling between the return and wound electrodes on the surface of the skin, sinking the surface current and force the wound current to travel deeper into the tissue. In the invention, the wound electrode(s) is positioned on a portion of the flexible substrate designed to be placed over wounded tissue and the return electrode is positioned on a portion of the substrate substantially surrounding the wound and guard electrodes and is designed to be placed over healthy tissue.

9 Claims, 3 Drawing Sheets

WOUND HEALING PATCH WITH GUARD ELECTRODES

CROSS-REFERENCE

This application claims priority from Provisional Application No. 60/863,417 filed Oct. 30, 2006, entitled Electrodes and Electronics for Electrostimulated Wound-Healing Devices which application is fully incorporated herein by reference.

The present invention is directed to a wound healing patch and, more particularly, to an improved wound healing patch using multiple electrodes, including wound healing, guard and return electrodes.

BACKGROUND OF THE INVENTION

Wounds and their complications are a major problem in both hospital and home settings. Healing such wounds is a priority for those who work in the health care field. There are many types of wounds that have different associated complications. For example, diabetic ulcers are caused and exacerbated by poor blood flow and inflammation, and are slow to heal, or may never heal if left untreated. This can lead to infection and scarring, among other problems. Thus, devices that promote wound healing are highly beneficial. While band aids and other wound dressings assist in the healing process by protecting the wound and helping to absorb fluids, it would be beneficial to have a wound healing patch which actively promotes the healing process.

SUMMARY OF THE INVENTION

In one embodiment, the present invention is directed to a wound-healing patch including a flexible substrate, at least one wound electrode at least one return electrode and at least one guard electrode positioned between the wound and return electrode. In this embodiment of the invention, the wound electrode(s) is positioned on a portion of the flexible substrate designed to be placed over wounded tissue. Further, in this embodiment of the invention, the return electrode(s) is positioned on a portion of the substrate remote from the wound-healing, electrode and designed to be placed over healthy tissue. In this embodiment of the invention, the guard electrode is positioned to be in the path of electrical current traveling from the return electrode to the guard electrode along the skin surface.

In a further embodiment of the present invention, the wound-healing patch includes a voltage source connected between the wound electrode(s) and the return electrode(s) with the voltage source being further connected between the guard electrode and the return electrode. In a further embodiment of the present invention the wound-healing patch includes a current source connected between the wound electrode(s) and the return electrodes(s) with a current source being connected between the guard and return electrodes. In a further embodiment of the present invention, the wound-healing patch includes a resistor connected to the wound electrode(s) and the guard electrode(s) to control the flow of current into the wound. In a further embodiment of the present invention the wound-healing patch includes control electronics adapted to control the flow of current through the wound electrode(s) and the guard electrode(s).

BRIEF DESCRIPTION OF THE FIGURES

The invention will now be described, by way of example only, with reference to the following figures. The accompanying drawings, which are incorporated herein and constitute part of this specification, illustrate presently preferred embodiments of the invention, and, together with the general description given above and the detailed description given below, serve to explain features of the invention, in which.

DETAILED DESCRIPTION OF THE FIGURES

The following detailed description should be read with reference to the drawings, in which like elements in different drawings are identically numbered. The drawings, which are not necessarily to scale, depict selected exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient", "host" and "subject" refer to any human or animal subject and are not intended to limit the systems or methods to human use, although use of the subject invention in a human patient represents a preferred embodiment.

Figure 1:
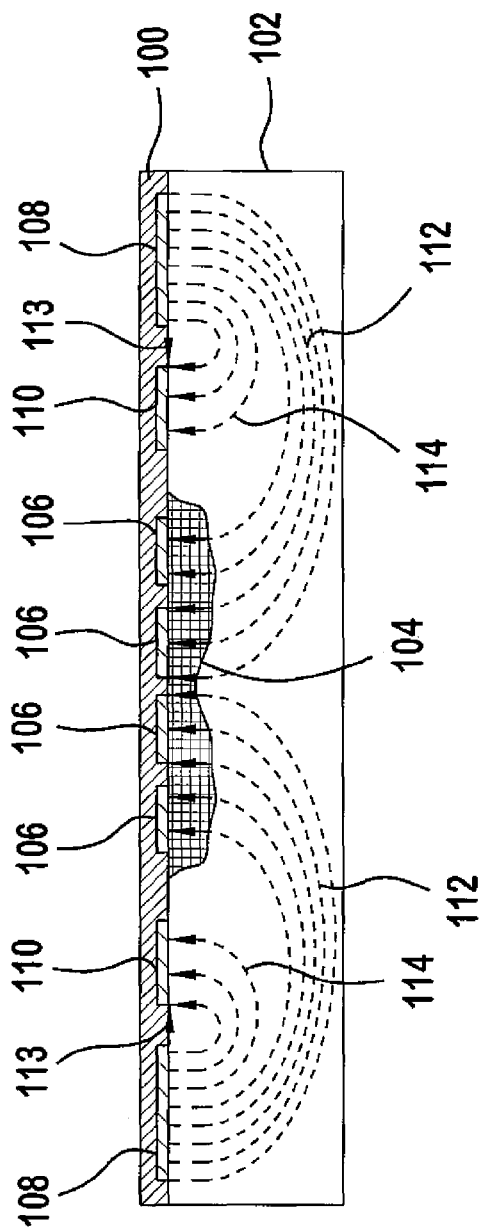
FIG. 1 illustrates an embodiment of the present invention, in cross section.

FIG. 1 illustrates a cross sectional view of an embodiment of the present invention. In the embodiment of the invention illustrated in FIG. 1, multiple wound electrodes 106 are positioned on patch 100. Patch 100 may be made of a polymer, for example. Wound electrodes 106 are positioned to cover wound 104. In this embodiment of the invention, return electrodes 108 are positioned on the outside area of patch 100. Return electrodes 108 are used to complete an electrical circuit through tissue 102 and wound 104. Further, in one embodiment of the invention, guard electrodes 110 are positioned between return electrodes 108 and wound electrodes 106. In operation, voltage is applied between return electrodes 108 and guard electrodes 110. In addition, voltage is applied between return electrodes 108 and wound electrodes 106. Patch 100 can be designed in such a way as to sink the skin surface current 113 and a portion of the current 114 traveling just below the surface, while maximizing wound current 112. Embodiments of present invention provide uniform current distribution through wound 104, enabling better wound healing. As illustrated by wound current 112, the electric field and current are substantially perpendicular to wound electrodes 106. The spatial distribution of wound electrodes 106 force current uniformly across wound 104, avoiding the creation of hot spots. Guard electrodes 110, also known as robber or sink electrodes, divert (or sink) current flow along the skin that could lead to a hot spot at the edge of wound 104. By using guard electrodes 110, current is forced to follow a deeper path through tissue 102, as illustrated by wound current 112. By following a deeper path through tissue 102, wound current 112 can potentially improve blood flow and wound healing in tissue 102. Wound electrodes 106, return electrodes 108, and guard electrodes 110 work together to shape electric field (and hence current flow) in tissue 102. As will be described in further embodiments, various means can be employed to preferentially direct or regulate current flow through tissue 102 and wound 104. For instance, current limiting circuitry can be used to limit flow through a particular electrode, such as guard electrode 110. In other embodiments, resistive components can be coupled with the electrodes to impede, or balance, current flow through the various electrodes. Drive circuitry can make very rapid adjustments to current flow, assuring uniform current flow across wound 104. Drive circuitry can be incorporated into patch 100, or can be part of a separate device that interfaces with patch 100. In the embodiment illustrated in FIG. 1, patch 100 is in direct contact with tissue 102, and can be fastened by way of pressure sensitive adhesive or by other means, such as removable straps. Patch 100 establishes electrical contact with tissue 102 via wound electrodes 106, return electrodes 108, and guard electrodes 110. When adhesives are used to bond patch 100 to tissue 102, the adhesive can be of a variety that is electrically conductive in the axis of current flow while not conductive in the lateral axis. Alternatively, the adhesive can be non conductive, and the area between the electrode and tissue can be free of adhesive, while the area between electrodes is covered with adhesive.

Taking a practical example of a circular patch, wound electrodes might cover an area of 5 cm in diameter to be useful for a wound up to about 5 cm in diameter. The individual wound electrodes might be circular in shape and have diameters of 1-10 mm; or they might be square or rectangular with linear dimensions of about 1-10 mm. The guard electrode might be a circular ring of width 1-10 mm and have a separation from the wound electrodes of less than 1 mm to more than 5 mm. Or the guard may be a ring comprised of a set of smaller electrodes, preferably of similar size to the wound electrodes. Generally, the separation or space between guard and wound electrodes should be low in order to force the current into the wound electrodes to travel substantially vertically. Different size wounds will require different size patches, and the arguments and logic herein can be extended to these different situations.

The electrical signal parameters (such as total current, current density, voltage, polarity, pulse width, duty cycle) can be adjusted according to wound size, phase of healing and other criteria. For example, current density (Amps/cm$^2$) through the wound is an important parameter, and might be adjusted to be between 0.1-10 μA/cm$^2$. This value can be adjusted by designing the appropriate current source, as shown in FIG. 3, or by adjusting voltage and resistance values in the voltage-drive configurations depicted in FIGS. 2, 5 and 6. Voltages necessary to achieve the desired current and current density, whether using a current-drive or voltage-drive configuration, may vary between 1 Volt and 500 Volts with 50-100 Volts being typical. The signal may be constant (DC) or time varying. Typically, time-varying, pulsed bi-phasic current is preferred for wound healing, because it can promote wound-healing while minimizing electrochemical effects at the interface of the electrodes and the tissue. The frequency may be between 0.1-100 Hz, with a square-wave profile preferred.

The guard electrode will preferably be electrically driven with similar parameters to the wound electrodes. For example, in a voltage-drive configuration, the voltage and series resistance for the guard might be the same as that of the wound electrodes.

Figure 2:
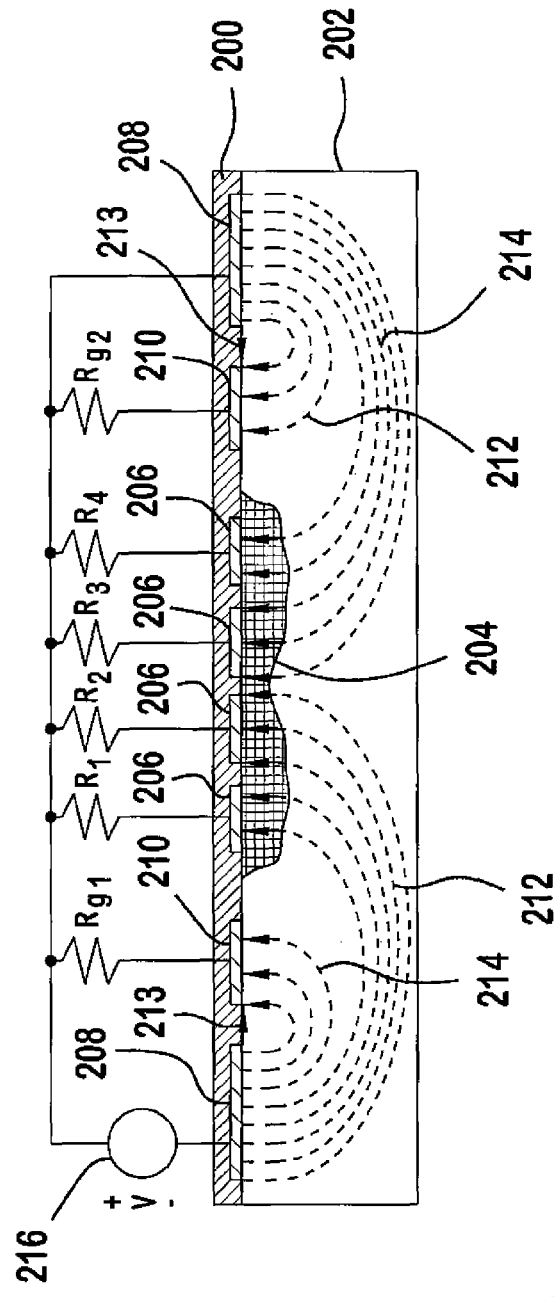
FIG. 2 illustrates an embodiment of the present invention wherein the electrodes are excited by a voltage source.
Figure 3:
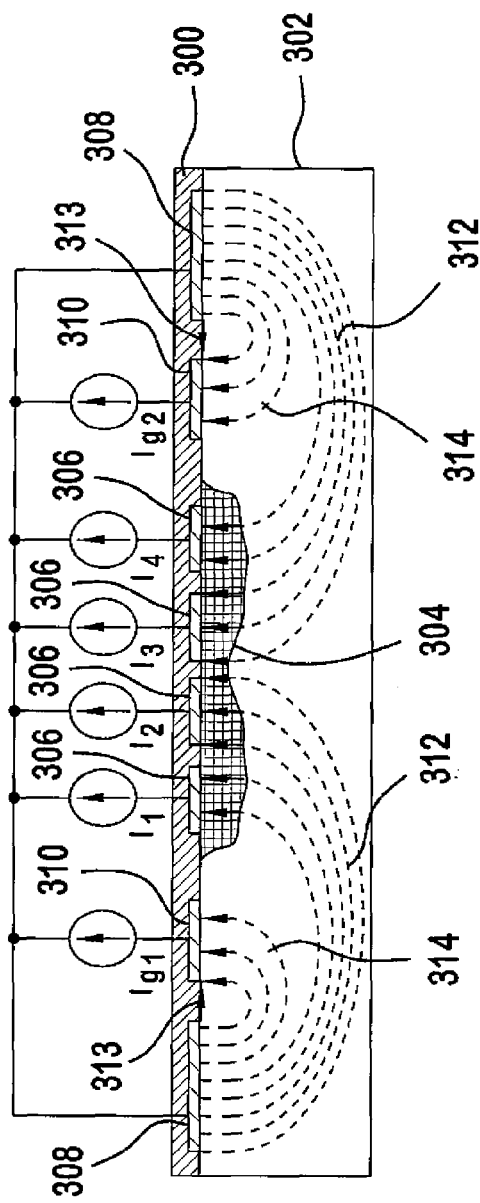
FIG. 3 illustrates an embodiment of the present invention wherein the electrodes are excited by a current source.

FIG. 2 illustrates an embodiment, patch 200, of the present invention that uses a voltage source. As illustrated in FIG. 2, when voltage source 216 is used, wound electrode resistors ($R_1, R_2 \ldots R_i$,) limit current flow through each wound electrode 206, while guard electrode resistors ($R_{g1}, R_{g2}$) limit current flow through each guard electrode 210. For example, if the wound electrode resistors are equal in value ($R_i=R$), and are large compared to the electrical resistance provided by tissue 202, then approximately equal current flow will flow through each wound electrode 206. Guard electrodes 210 absorb lateral current that travels along and near to the skin surface, as illustrated by current 213 and some of the current 214 traveling just below the surface. Guard electrodes 210 ensure that current reaching wound 204 follows a longer, deeper path, flowing substantially vertically through wound 204 from tissue 202. Wound current 212 and skin surface current 214 illustrate the current distribution using wound electrodes 206, return electrodes 208, and guard electrodes 210, according to the present invention. In this embodiment of the present invention, the current density (Amps/cm$^2$) is substantially the same from point to point across wound 204. Furthermore, since current reaching wound 204 is forced to flow through deeper lying tissue and blood vessels, embodiments according to the present invention increase interaction between wound 204 and deeper-lying tissue and blood vessels, potentially facilitating wound healing through such mechanisms as increased transport of cells and biochemical agents. In a further embodiment of the present invention, wound electrodes 206 cover an area larger than wound 204, and guard electrodes 210 are not necessary since the outer edges of wound electrodes 206 can serve the same function as guard electrodes 210.

An advantage of using wound-healing patches according to the present invention is that they can enable the use of higher current than other configurations. Since current density is uniform across the wound, current can be increased without causing "hot spots", areas of high current density that can adversely affect tissue and wound healing.

Figure 4:
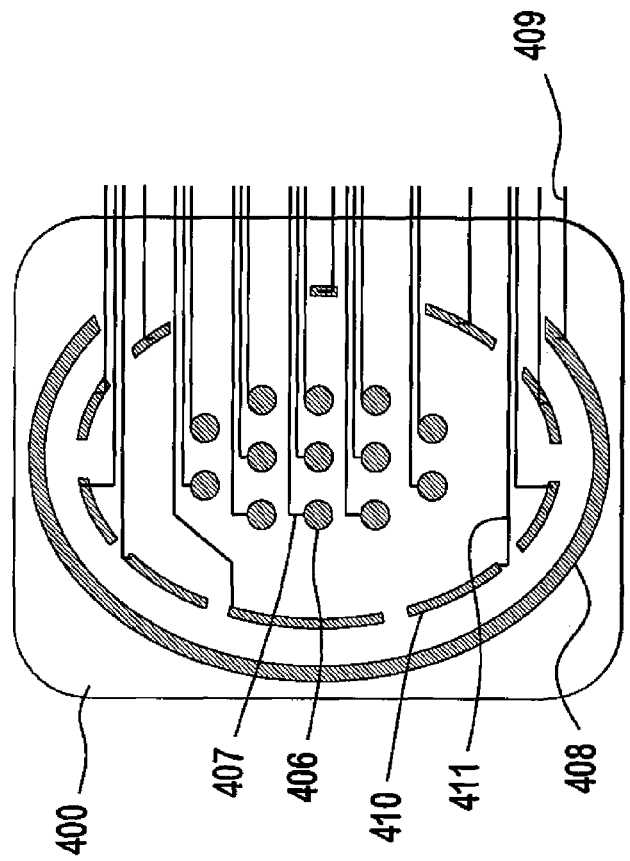
FIG. 4 is a top view of a patch according to the present invention, looking through the thickness of the patch to an array of electrodes.

FIG. 3 illustrates an embodiment of the invention that uses multiple current sources. The embodiment of the invention illustrated in FIG. 3 uses current sources ($I_{g1}, I_{f}, \ldots$) rather than a voltage source and resistors. Current sources can be made with a few transistors, discrete or integrated onto an ASIC (application-specific integrated circuit) for example. In a further embodiment of the present invention, electronic components and conductive traces are isolated such that only wound electrodes 306, return electrodes 308, and guard electrodes 310 will make electrical contact with wound 304 and tissue 302. Patch 300 can be designed in such a way as to sink the skin surface current 313 and a portion of the current 314 traveling just below the surface, while maximizing wound current 312. FIG. 4 is a top view of patch 400 according to the present invention, looking through the thickness of patch 400 to an array of wound electrodes 406, return electrode 408, and an array of guard electrodes 410. Wound electrode trace 407, return electrode trace 409, and guard electrode trace 411 on patch 400 are electrically isolated from each other (encapsulated in polymer for example) to prevent shunting or shorting of current away from wound electrodes 406, return electrode 408, and guard electrodes 410. In embodiments of the present invention, electrodes can be made using various materials. Electrodes can be screen-printed using conductive inks, such as inks containing carbon, silver, silver chloride, or other conductive materials. Alternatively, electrodes can be sputtered or plated metal, or other conductive material, such as indium tin oxide. A wide range of materials and processes can be used to make electrodes according to the present invention, as long as the electrodes are conductive and compatible with tissue and wounds.

Figure 5:
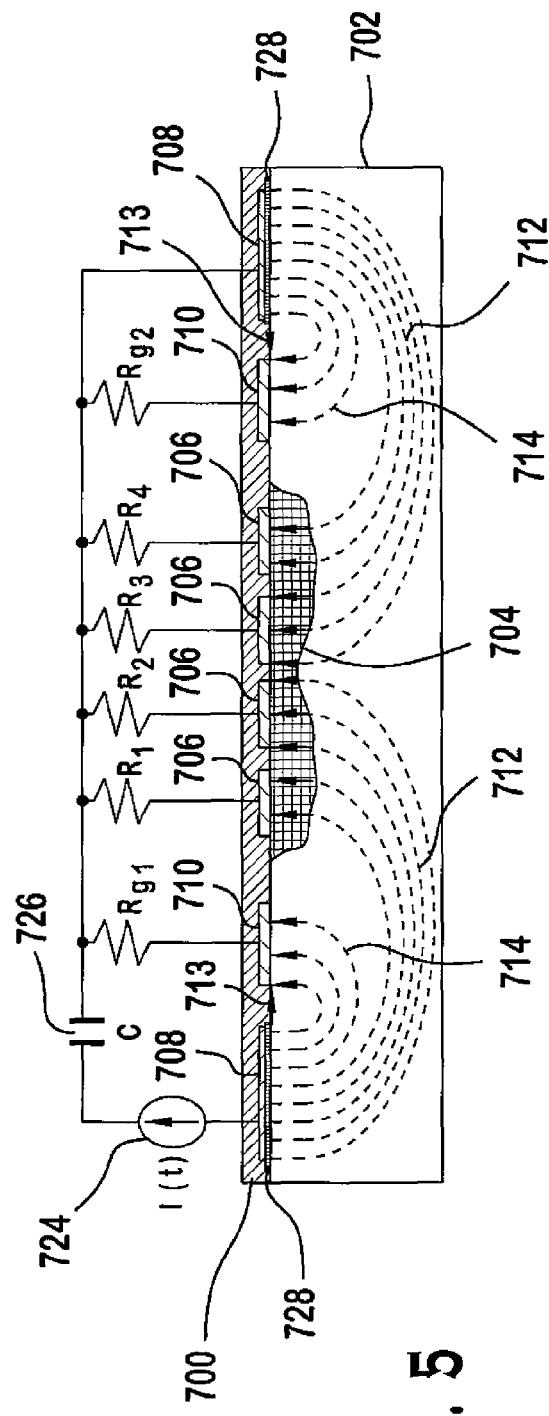
FIG. 5 illustrates an embodiment of the present invention where wound and guard electrodes are in direct contact with tissue, while return electrodes are electrically insulated from tissue.

In FIG. 5, an embodiment of the present invention includes wound electrodes 706 and guard electrodes 710 in direct contact with wound 704 and tissue 702, while return electrodes 708 are electrically isolated from tissue 702 by including insulators 728. In this embodiment, time-varying current source 724 moves charge through wound 704, through wound electrodes 706, and into capacitor 726. Patch 700 can be designed in such a way as to sink the skin surface current 713 and a portion of the current 714 traveling just below the surface, while maximizing wound current 712. The embodiment of the invention illustrated in FIG. 5 uses capacitive coupling through insulators 728 to couple the electric field from current source 724. Capacitor 726 becomes charged over time, as does tissue 702. If the charge transferred from tissue 702 into capacitor 726 is very small compared to the total charge in tissue 702, the voltage potential of tissue 702 will change only slightly. The charge in tissue 702 will be neutralized, in time, by ions in the air, and by charge transfer to other objects. Current source 724 provides variable current over time, while resistors $R_{g1}$, $R_1$ through $R_4$, and $R_{g2}$ balance current flow through tissue 702 and wound 704. Capacitor 726 also serves to block unwanted direct current, only allowing time varying current to pass. Embodiments of the present invention that incorporate insulating material between the electrodes and tissue 702 or wound 704 are particularly useful in minimizing undesirable interactions between electrodes and tissue 702 and/or wound 704. Insulators 728 prevent electrochemical interactions with tissue 702 and/or wound 704 that could lead to hydrolysis or other reactions, preventing the creation of undesirable byproducts and physical changes, such as changes in pH.

Figure 6:
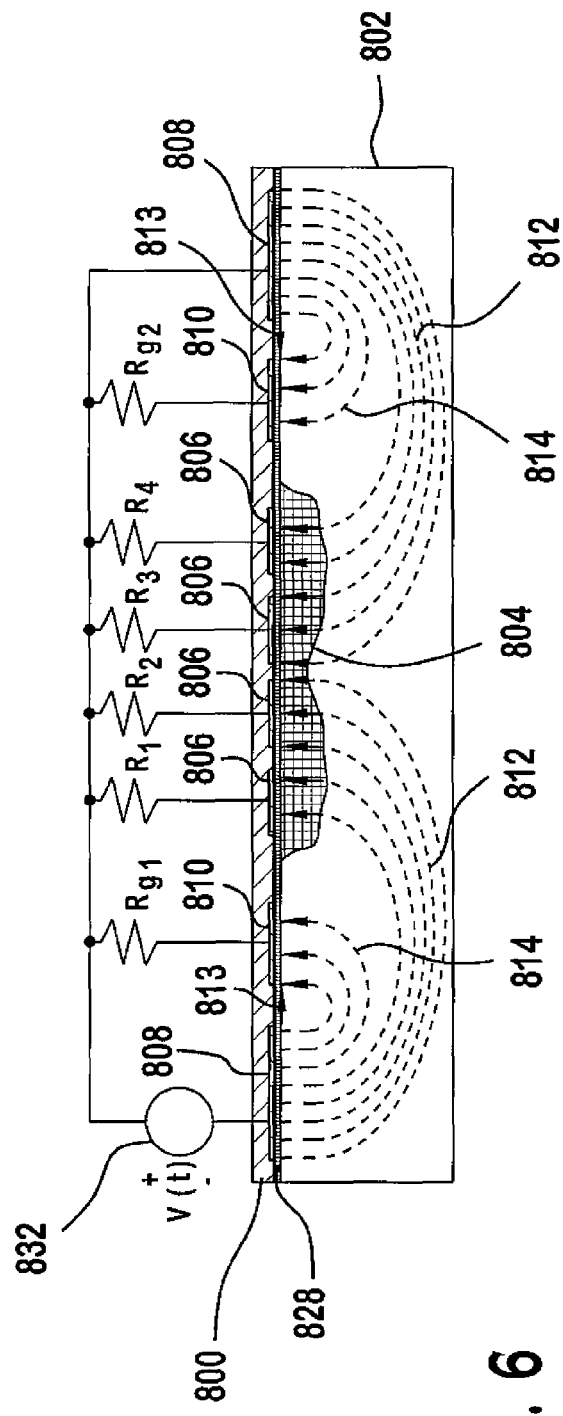
FIG. 6 illustrates an embodiment of the present invention where wound, guard, and return electrodes are electrically insulated from tissue.

FIG. 6 illustrates another embodiment of the present invention, wherein patch 800 has insulator 828 between tissue 802, wound 804, wound electrodes 806, return electrodes 808, and guard electrodes 810. Patch 800 can be designed in such a way as to sink the skin surface current 813 and a portion of the current 814 traveling just below the surface, while maximizing wound current 812. The embodiment of the invention illustrated in FIG. 6 is similar in structure as the embodiment illustrated in FIG. 2, with the addition of an insulator between the electrodes, the tissue, and the wound. In the embodiment illustrated in FIG. 8, voltage source 832 is time dependent (shown here as V(t)), while wound current 812 and skin surface current 814 are time dependent as well.

In a further embodiment of the present invention, alternating current or voltage may be used to force electrical current through the wound. In this embodiment, one or more wound electrode(s) is positioned over the wound, but no DC return electrode is provided. In this embodiment of the invention, electrical power, such as a voltage or current drive, would force AC or transient charge in and out of the wound through the wound electrode(s). A capacitor or super capacitor could be used to store accumulated charge. In some designs, an electrically isolated return electrode could be used to capacitively couple the charge in and out of the wound, but no net charge transfer would occur.

In some embodiments of the present invention, the signal can be varied over each part of the wound, to optimize wound healing.

In other embodiments of the present invention, measuring the electrical characteristics of the wound can assess the efficacy and rate of wound healing. Measurement circuitry can be connected to wound, return, or guard electrodes, and can measure physical parameters, such as temperature. A variety of circuitry can be used to measure temperature, including thermocouples and RTDs (resistance temperature device). RTDs can be made from resistive traces in the patch that change resistivity with temperature. Measurement of voltages, currents and electrical fields (voltage gradient), along with temperature inside and outside the wound, provides useful information for the patient and/or the health care provider.

In further embodiments of the present invention, impedance ratios may be measured using a wound-healing patch. The impedance is the ratio of applied voltage to current, each of which may be time varying. The impedance is a complex quantity (has real and imaginary components, or equivalently, magnitude and phase) and depends on frequency. Impedance parameters of the wound can be measured with electrodes and the proper electronics (on or off the patch). Two-wire or 4-wire configurations can be used to measure resistance and impedance. Impedance can be measured between any independent electrodes, including the return and wound electrodes.

In further embodiments of the present invention, wound-healing devices can also include different types of sensors to assess wound healing and the potential of infection. Sensors may measure chemicals, such as oxygen or VOCs (volatile organic compounds) that are exuded by infected wounds. Sensors could also measure the pH of the wound, or the wounds optical properties, such as reflection, and/or absorption and emission of light in the microwave, visible, infrared, or ultraviolet spectrums.

In further embodiments of the present invention, wound-healing assessment information can be relayed to the user or doctor with an electronic display, onboard or external to the patch. This might be a digital display (e.g., the LCD of a PDA) on the patch or external to it, or indicators on the patch such as LEDs (or organic LEDs).

In further embodiments of the present invention, wireless methods may be used to transmit data and power. A patch may include one or more antennas for this purpose, including coil antennas for inductive coupling, dipole antennas, phased arrays etc. Power can be coupled into the wound-healing patch inductively, for example. This scheme would permit a reliable, robust, waterproof power connector to be made with coil antennas that are fully encased in plastic, for example.

In further embodiments of the present invention, wireless telemetry can be used to transmit data into and from the wound-healing patch. Data from the patch can be transmitted to a receiver that displays data or relays it to a health-care professional who can make recommendations that are then transmitted back to the patient or directly to the wound-healing device to modify its operational parameters. Methods of telemetry that can be used include short-distance methods (such as inductive coupling and impedance modulation) and longer-distance transmission protocols such as AM, FM, cellphone, GSM, TDMA, 1XRTT, CDMA, EDGE, Bluetooth, Zigbee, 802.11a/b/g.

In further embodiments of the present invention, electronic functions can be housed on the patch or off the patch. This may include one or more ASICs. In other embodiments of the present invention, electronic signal can be made to vary over the wound area. That is, non-uniform current or voltage can be generated over the wound rather than uniform current density. In other embodiments of the present invention, feedback can be used to adjust the electric signal as the wound healing progresses. E.g., the current can be reduced in areas where healing is more complete. The signal can also be adjusted depending on the phase of healing (inflammation, proliferation, reconstruction etc). Completely different signals and polarity may be appropriate for the different phases. In other embodiments of the present invention, the short-term temporal profile of the voltage or current drive can be DC or AC, including sinusoidal, square wave, pulsed (<50% duty cycle), triangular, sawtooth, or tone burst profiles.

In further embodiments of the present invention, data can be displayed to the user and communicated to and from health-care professionals as part of the monitoring and control process. Communication might be via lights or displays mounted on a patch, or through wired or wireless transmission to/from nearby or distant locations. For example, in one embodiment of the present invention, simple data might only trigger a light on the patch that alerts the user to change the wound-healing patch. In another embodiment, data could be transmitted to a computer in the doctor's office that performs an analysis and warns of an infection in real time or with a short time delay. Self-test and calibration can be integrated into the system and performed upon initial application of the patch and at periodic intervals.

The present invention is particularly beneficial because multiple-electrode designs enable controlled delivery and measurement of electrical signals at each part of a wound. In a wound-healing patch according to the present invention, it is possible to apply equal or varied current density through all parts of a wound. Further, utilizing a patch according to the present invention, it is possible to ensure that current travels from deep tissue through the wound to the surface, substantially perpendicular to the surface, thus facilitating interaction with the deep healthy tissue and blood supply. Further, utilizing a wound-healing patch according to an embodiment of the present invention, it is possible to measure electrical and other wound parameters to assess healing. Further, in another embodiment of the present invention, it is possible to tailor the electrical signal (current or voltage) applied to each part of a wound to optimize local healing.

In any of these dressing designs, it may be advantageous to have the collective area of the wound electrodes smaller than that of the return electrodes. This causes the current density (A/cm$^2$) and electric field to be highest in the tissue near the wound electrodes (i.e., in the wound itself). Another way to say this is that most of the applied voltage will appear across the smaller electrodes, i.e., between the wound electrodes and the tissue, rather than between the return electrodes and the tissue. This result follows directly from Ohm's law, which states that for a given material of resistivity $\rho$ (ohm-cm), higher current density results in stronger electric field: $E=\rho J$, where E is the electric field (V/cm) and J is the current density (A/cm$^2$). This configuration could be used to maximize the efficacy of wound-healing while minimizing the energy drain of a battery or other power source.

The present invention is directed to wound-healing patches (bandages) with integrated electrodes, electronics and electrostimulation. Embodiments of the present invention employ multiple, independent electrodes covering the wound, wherein the electrodes can be used to deliver electrical signals, and can be used to measure electrical wound parameters. "Independent electrode" means an electrode that can be controlled separately from surrounding electrodes, including the ability to have a different electrical voltage or current than nearby electrodes. Control may be local and simple, as in a series resistor that limits electrode current while many electrodes are connected to the same voltage source (FIG. 2). Control may also be remote, with electronic circuitry off the patch. "Independent electrode" also includes electrodes that operate partially independently. Electrical wound parameters can be used to assess healing progress, as well as to tailor the signals applied to the wound in a closed-loop system that optimizes the healing process (rate, scarring, etc.). The system can also control and optimize non-electrical functions integrated into the patch, such as drug delivery and environmental control (oxygen, humidity and temperature).

While preferred embodiments of the present invention have been shown and described herein, it will be obvious to those skilled in the art that such embodiments are provided by way of example only. Numerous variations, changes, and substitutions will now occur to those skilled in the art without departing from the invention. Various alternatives to the embodiments of the invention described herein may be employed in practicing the invention. It is intended that the following claims define the scope of the invention and that methods and structures within the scope of these claims and their equivalents be covered thereby.

What is claimed is:

1. A wound-healing patch comprising:
   a flexible substrate;
   at least one wound electrode positioned on a portion of said flexible substrate adapted to be placed over a wounded tissue;
   at least one return electrode positioned on said substrate remote from said wound-healing electrode, wherein said return electrode is positioned on a portion of said substrate adapted to be place over healthy tissue; and
   at least one guard electrode positioned between said at least one of said wound electrodes and at least one of said return electrodes.

2. A wound-healing patch according to claim 1 further comprising a voltage source connected between at least one of said wound electrodes and at least one of said return electrodes, said voltage source being further connected between said return electrode and said guard electrode.

3. A wound-healing patch according to claim 1 further comprising a current source connected between at least one of said at least one wound electrode and at least one of said at least one return electrodes.

4. A wound-healing patch according to claim 1 further comprising at least one resistor connected to at least one of said at least one wound electrode and said guard electrode.

5. A wound-healing patch according to claim 1 further comprising control electronics adapted to control the flow of current through said at least one wound electrode, guard electrode and return electrode.

6. A wound-healing patch according to claim 1 wherein one of said at least one wound-healing electrode, said guard electrode or said at least one return electrode is electrically isolated from tissue when said patch is attached to said tissue.

7. A wound-healing patch according to claim 1 wherein said at least one wound-healing electrode, said at least one guard electrode and said at least on return electrode are electrically isolated from tissue when said wound-healing patch is attached to said tissue.

8. A wound-healing patch according to claim 7 wherein at least one said wound electrode, said at least one guard electrode or said at least one return electrode are isolated from said tissue by a distributed resistive element.

9. A wound-healing patch according to claim 1 wherein said at least one electrode form a ring substantially surrounding said guard electrodes and said wound healing electrodes.

* * * * *